(12) United States Patent
Daniels, Jr. et al.

(10) Patent No.: US 7,914,498 B2
(45) Date of Patent: Mar. 29, 2011

(54) SELF-SUTURING CATHETER SYSTEM

(76) Inventors: Richard D Daniels, Jr., Zephyrhills, FL (US); Cynthia B Daniels, Zephyrhills, FL (US); Robert C. Brown, Tallahassee, FL (US)

( * ) Notice: Subject to any disclaimer, the term of this patent is extended or adjusted under 35 U.S.C. 154(b) by 79 days.

(21) Appl. No.: 12/315,774

(22) Filed: Dec. 5, 2008

(65) Prior Publication Data
US 2010/0145279 A1 Jun. 10, 2010

(51) Int. Cl.
*A61M 5/32* (2006.01)

(52) U.S. Cl. .......................................... 604/174; 606/139

(58) Field of Classification Search .......... 604/158–163; 606/139, 144–148
See application file for complete search history.

(56) References Cited

U.S. PATENT DOCUMENTS

| 4,345,601 A * | 8/1982 | Fukuda .......................... 606/147 |
| 4,547,194 A | 10/1985 | Moorehead |
| 4,578,061 A | 3/1986 | Lemelson |
| 4,650,473 A * | 3/1987 | Bartholomew et al. ........ 604/174 |
| 4,798,595 A * | 1/1989 | Andersson et al. ............ 604/174 |
| 4,850,960 A * | 7/1989 | Grayzel ......................... 604/510 |
| 5,312,345 A | 5/1994 | Cole |
| 5,792,115 A * | 8/1998 | Horn .............................. 604/174 |
| 2003/0163097 A1 * | 8/2003 | Fleury et al. .................. 604/263 |
| 2007/0167970 A1 * | 7/2007 | Sonoda et al. ................ 606/185 |

* cited by examiner

*Primary Examiner* — Nicholas D Lucchesi
*Assistant Examiner* — Gerald Landry, II
(74) *Attorney, Agent, or Firm* — Robert C. Brown

(57) ABSTRACT

An improved catheter system having a hub including a self-suturing mechanism comprising a circular needle rotatably slidable in a circular groove in the hub. The needle is sharpened to a point at an end and preferably is also formed into a tang for use as a handle. The hub is flattened on a side to be adjacent to the skin, defining a hub flat thus truncating the groove through, for example, 60° thereof. After the catheter is positioned in the blood vessel, the flat is pressed against the skin. The circular needle is rotated through an angle such that the circular needle passes through a portion of the skin, thereby "self-suturing" the hub to the skin of the patient. The hub is thus firmly attached to the patient, and no separate suturing is required. De-suturing of the catheter requires only reverse rotation of the circular needle.

14 Claims, 3 Drawing Sheets

SELF-SUTURING CATHETER SYSTEM

TECHNICAL FIELD

The present invention relates to catheter systems for introducing medication into vascular systems; more particularly, to intravenous catheter systems; and most particularly, to an improved intravenous catheter-over-needle system having a non-linear, pivotable, preferably circular needle for self-suturing of a catheter hub to skin at a point of catheter tube insertion without requiring separate suturing to maintain the catheter tube in place.

BACKGROUND OF THE INVENTION

Catheter-over-needle (CON) and catheter-over-wire (COW) systems are well known in the medical arts for introducing medication or other treatments into the vascular systems of animals. A typical prior art CON system, such as the MILACATH™ Extended Use CON, available from MILA International, Inc., Erlanger, Ky., USA, comprises a flexible catheter tube (also referred to herein generically as a "catheter") mounted to a hollow catheter hub structure having laterally extending perforated wings. As delivered, the system includes a hollow rigid insertion needle extending through the hub and catheter to facilitate insertion of the catheter through the skin and into an underlying blood vessel. Appearance of blood at the outer end of the needle indicates that the catheter and needle are emplaced within the blood vessel. The needle is then withdrawn and discarded, and the catheter is advanced to a desired distance within the blood vessel. The perforated hub wings are then sutured conventionally to the skin to keep the catheter from being forced out of the vein.

Some other prior art catheter systems employ other components to assist in emplacement of the catheter, such as a guide wire in COW systems, but the basic principles of emplacement are the same.

A well-known operational problem in the use of prior art catheter systems is the difficulty and time consumed in suturing the catheter hub to the skin. This can be especially troublesome in veterinary applications wherein the animal patient may be large, active, and/or dangerous, and time is of the essence.

What is needed in the art is an improved catheter system wherein means for mechanically attaching a catheter hub to the skin of a patient are included in the system.

It is a principal object of the present invention to obviate the need for separately suturing a catheter hub to the skin of a patient.

It is a further object of the invention to facilitate, and to shorten the overall time required for, intravascular installation of a CON catheter.

SUMMARY OF THE INVENTION

Briefly described, a prior art catheter system comprises a flexible catheter tube to cooperating with a catheter hub. The tube extends some distance in a patient's vein, and the hub remains outside the patient, typically attached to the patient's skin by sutures of thread. The system may further include an insertion needle or wire extending through the hub and catheter tube to facilitate insertion of the catheter, but such a needle or wire is incidental to the present invention which is directed specifically to an improved catheter hub.

The present invention consists in an improved catheter hub comprising a self-suturing mechanism for attaching the hub to the skin of a patient. The self-suturing mechanism includes a non-linear suturing needle, pivotably attached to the hub, which is easily rotated by an operator to engage an adjacent portion of the patient's skin. In a currently-preferred embodiment, a circular needle is rotatably slidable in a circular groove in the hub. The axis of the groove and needle may be coaxial with the axis of the catheter or may be transverse thereto. Preferably, the needle is curved through more than 180° but less than 360° and is sharpened to a point at a first end and is formed into a tang at the opposite end. Alternatively, the hub may comprise first and second circular grooves disposed around a transverse axis and on opposite sides of the catheter/hub axis. In such an embodiment, the circular needle may comprise first and second circular portions disposed respectively in the first and second circular grooves and connected by a connecting tang. In either embodiment, the hub preferably is flattened on a side to be adjacent to the skin, defining a hub flat truncating the groove or grooves through for example 60° thereof. The needle occupies preferably the same or slightly fewer degrees of arc as the truncated groove such that, during insertion of the CON system into a blood vessel, preferably neither the needle point nor the tang extends beyond a hub boundary plane defining the flatted portion. After the catheter is properly positioned in the blood vessel, the flat is pressed against the skin. The operator engages the tang, preferably with the ball of the thumb, and rotates the circular needle in the groove through an angle preferably greater than the central angle subtended by the flat, such that the point of the circular needle passes beyond the boundary flat through a portion of the skin and then returns to the circular groove, thereby "self-suturing" the hub to the skin of the patient. The hub is thus firmly attached to the patient, and no separate conventional suturing is required. Removal of the catheter requires only reverse rotation of the non-linear self-suturing needle to the starting position to free the skin, followed by withdrawal of the catheter from the blood vessel in known fashion.

BRIEF DESCRIPTION OF THE DRAWINGS

The present invention will now be described, by way of example, with reference to the accompanying drawings, in which.

Corresponding reference characters indicate corresponding parts throughout the several views. The exemplifications set out herein illustrate currently preferred embodiments of the invention, and such exemplifications are not to be construed as limiting the scope of the invention in any manner.

DESCRIPTION OF THE PREFERRED EMBODIMENTS

Figure 1:
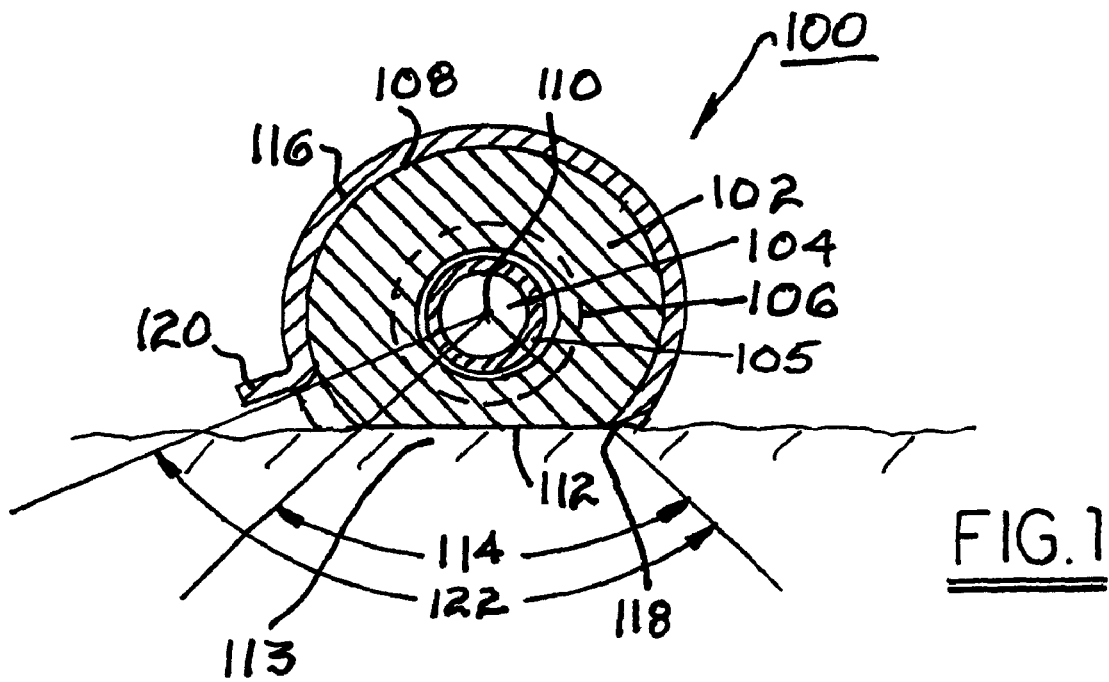
FIG. 1 is a cross-sectional view of a first embodiment of an improved intravenous catheter system having a rotatable circular suturing needle, showing the needle in the ready position.

Referring to FIG. 1, in a first preferred embodiment 100 of an improved intravenous catheter system, a catheter hub 102 includes a central opening 104 for passage of a wire, catheter tube, blood, and/or medications, as well as for an optional insertion needle 105 as is known in the prior art. Opening 104 is coaxial with a catheter tube 106 attached to hub 102 in a CON system. Hub 102 further includes a circular groove 108 surrounding the axis 110 of hub 102. Circular groove 108 may or may not be coaxial with opening 104. A flatted portion 112 defining a flat side of hub 102 truncates hub 102 and circular groove 108 through a central truncation angle 114. In use of system 100, flat side 112 rests against a patient's skin 113. A circular needle 116 ending in a sharp point 118 and an opposite-end tang 120 is slidably disposed in circular groove 108. Needle 116 preferably is curved through a central angle greater than 180°, the complementary central angle 122 preferably being greater than central truncation angle 114. Thus, when system 100 is placed for use against a patient's skin 113, preferably neither point 118 nor tang 120 projects initially beyond a plane containing flat side 112.

Figure 2:
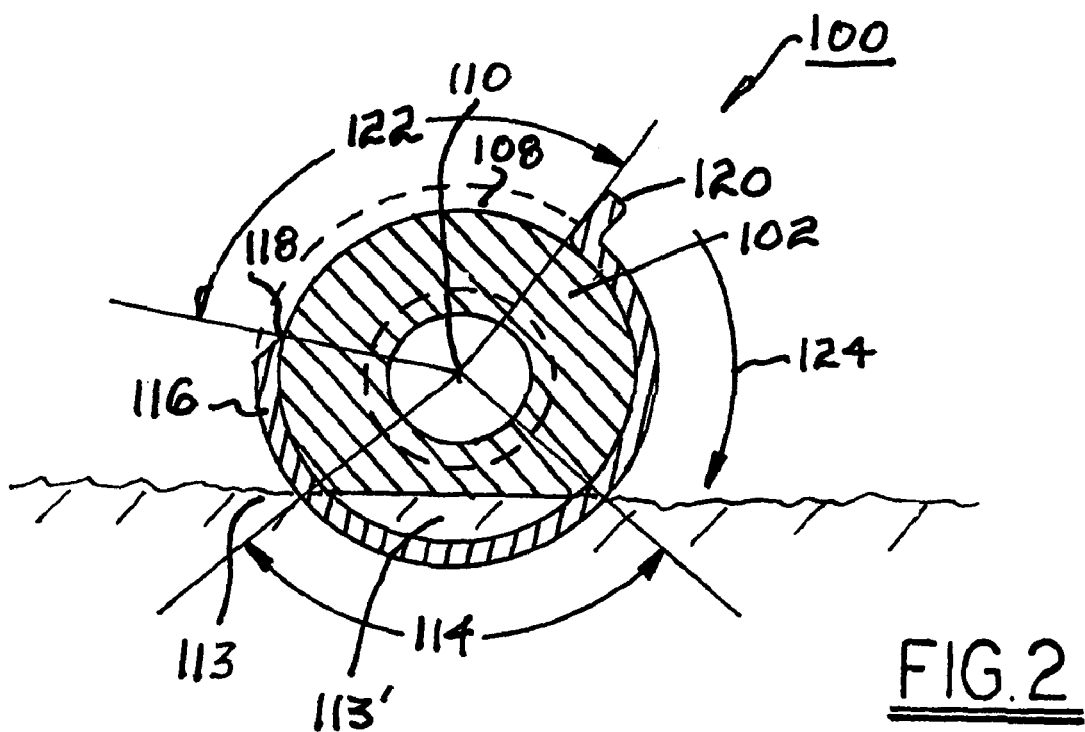
FIG. 2 is a cross-sectional view of the first embodiment shown in FIG. 1, showing the needle in the sutured position.

In use as in a CON system, insertion needle 105 and catheter tube 106 are inserted together through skin 113 in known fashion until proper entry of needle 105 into a target blood vessel (not shown) is indicated by the appearance of blood at the outer end of insertion needle 105. Insertion needle 105 is then withdrawn and discarded. Catheter tube 106 may be inserted farther into the blood vessel as may be desired. When the catheter is properly situated, flat side 112 is pressed into firm contact with skin 113. Referring to FIG. 2, tang 120 is engaged by the operator such as by the ball of the operator's thumb, and circular needle 116 is rotated in direction 124 in groove 108 about axis 110 from the non-suture position shown in FIG. 1 to the suture position shown in FIG. 2, causing point 118 to follow a circular path through skin 113, thereby capturing a skin portion 113'. Hub 102 is now firmly sutured to patient skin 113, thereby holding catheter 106 in correct position without resort to supplementary suturing as in the prior art. Removal of catheter 106 requires only reverse rotation of the circular needle to the starting position to free the skin, followed by withdrawal of the catheter tube from the blood vessel.

Figure 3:
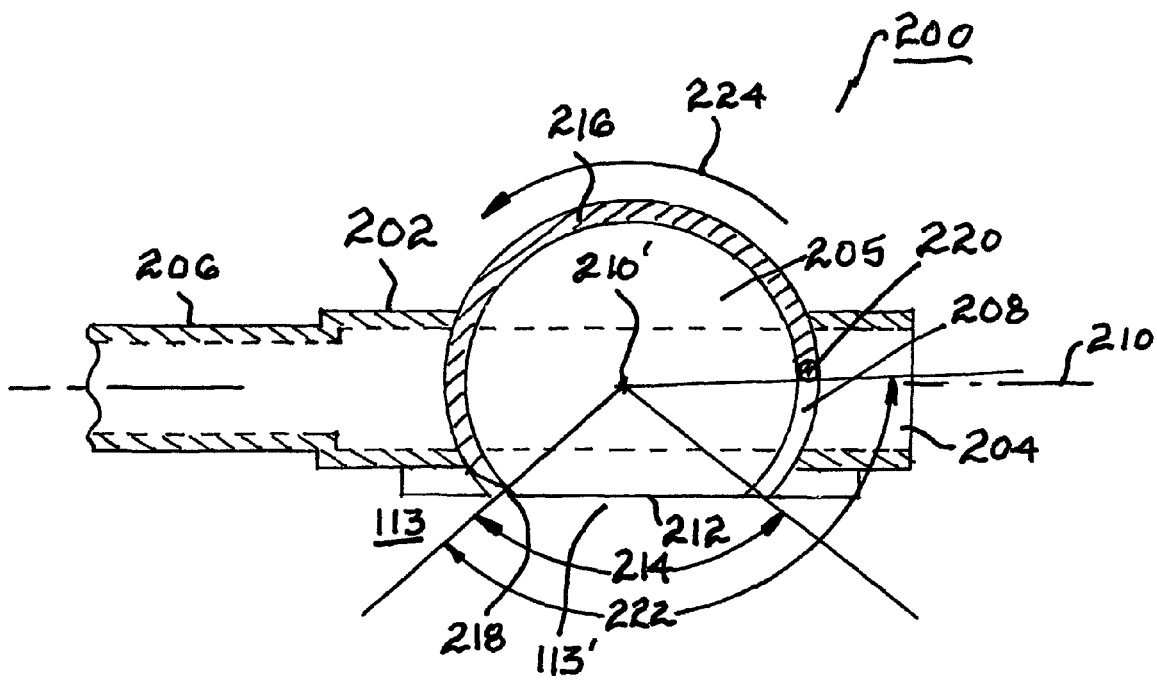
FIG. 3 is a cross-sectional view of a second embodiment of an improved intravenous catheter system having a rotatable two-portion circular suturing needle, showing the needle in the ready position.
Figure 4:
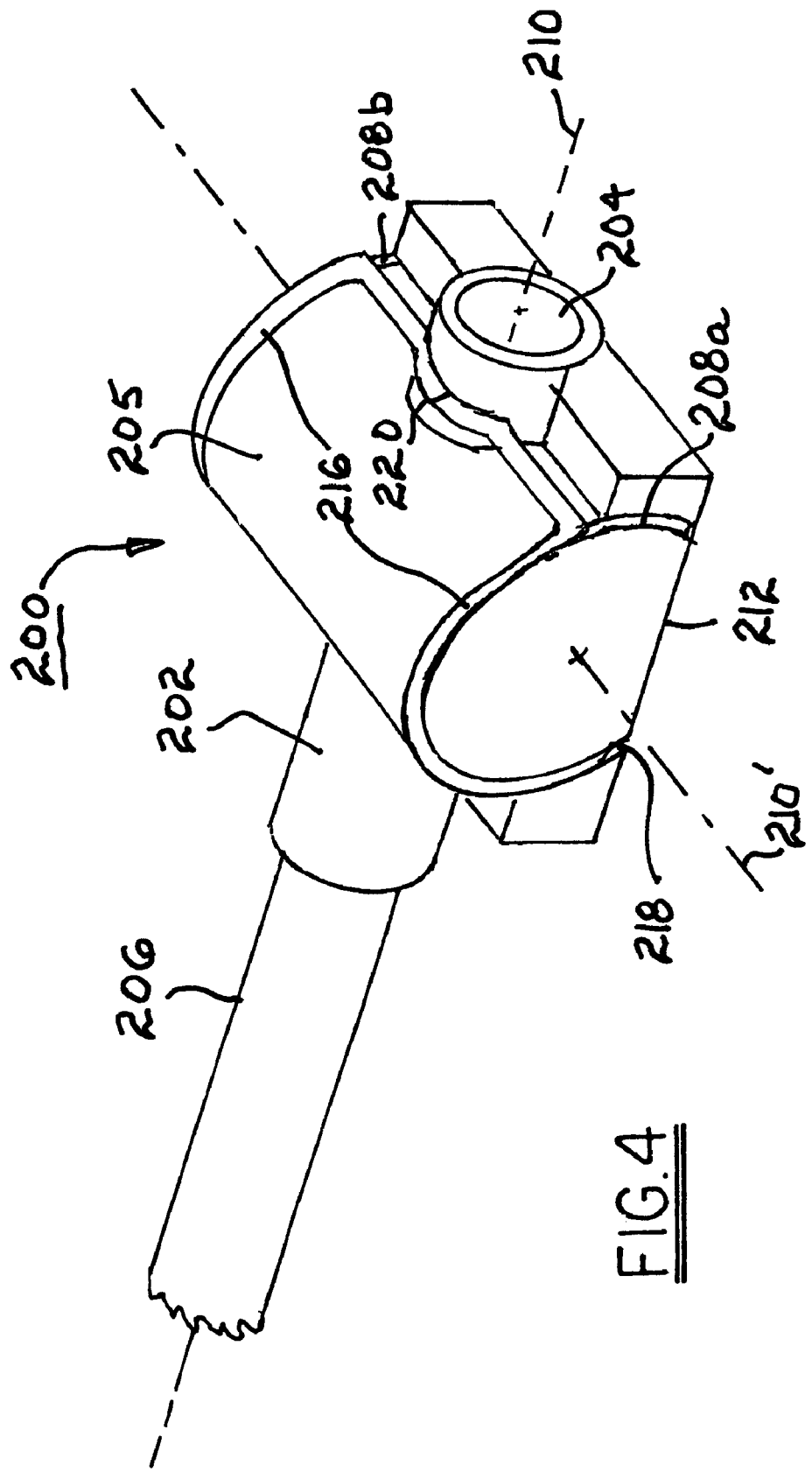
FIG. 4 is an isometric view of the second embodiment shown in FIG. 3.

Referring now to FIGS. 3 and 4, in a second embodiment 200 of an improved intravenous CON system, a catheter hub 202 includes a central opening 204 for passage of blood and/or medications, as well as for an optional insertion needle (not shown) or wire or catheter tube in a COW system (not shown). Opening 204 is coaxial with a catheter 206 attached to hub 202. Hub 202 further includes a structure 205 having first a second circular grooves 208a, 208b surrounding an axis 210' transverse to axis 210 of hub 202. Axis 210' may or may not intersect axis 210. A flatted portion 212 defining a flat side of hub 202 truncates hub 202 and circular grooves 208a, 208b through a central truncation angle 214. In use of system 200, flat side 212 rests against a patient's skin 113. A needle 216, comprising first and second circular portions, each ending in a sharp point 218 (only one point visible in FIGS. 3 and 4), and a connecting tang 220, is slidably disposed in circular grooves 208. Needle 216 is curved through a central angle greater than 180°, the complementary central angle 222 preferably being greater than central truncation angle 214. Thus, when system 200 is placed for use against a patient's skin 113, preferably neither of points 218 projects initially beyond a plane containing flat side 212.

Insertion of system 200 is similar to that described above for system 100. When the catheter is properly situated in the blood vessel, flat side 212 is pressed into firm contact with skin 113. Connecting tang 220 is engaged by the operator such as by the ball of the operator's thumb and is pushed forward, causing circular needle 216 to be rotated in direction 224 in grooves 208a, 208b about axis 210', causing points 218 to follow circular paths through skin 113, thereby capturing a skin portion 113' within the scope of each needle portion. Hub 202 is now firmly sutured to the patient skin 113 on either side of catheter/hub axis 210, thereby holding catheter 206 in correct position without resort to supplementary suturing as in the prior art. Removal of catheter 206 requires only reverse rotation of the non-linear suturing needle to the starting position to free the skin, followed by withdrawal of the catheter from the blood vessel.

Either of hubs 102/202 may be readily formed as by injection molding of a thermoplastic, as is known in the prior art, with grooves 108/208a/208b molded therein. Circular needles 116, 216 may be readily formed by bending and sharpening of appropriately tempered wire stock, and may be resiliently deformed slightly to snap into grooves 108/208a/208b during assembly of systems 100/200. Because each circular needle 116/216 extends through a central angle greater than 180°, the needles are retained by spring force like spring clips within their respective grooves. Preferably, friction between the non-linear needles and the hub keeps the needles from spontaneously de-suturing.

While the invention has been described by reference to various specific embodiments, it should be understood that numerous changes may be made within the spirit and scope of the inventive concepts described. Accordingly, it is intended that the invention not be limited to the described embodiments, but will have full scope defined by the language of the following claims.

What is claimed is:

1. A catheter hub, comprising:
    a) a hub structure having a central opening having an axis, said hub being coaxially joinable to said catheter tube, and said opening allowing passage of fluids therethrough during use of said catheter hub and said catheter tube; and
    b) a solid suturing needle slidably rotatable on said hub for attaching said hub structure to a portion of said patient's skin, said suturing needle forming more than 180° of a full circle such that said suturing needle is permanently disposed on said hub structure.

2. A catheter hub in accordance with claim 1 wherein said suturing needle is non-linear.

3. A catheter hub in accordance with claim 2 comprising:
    a) at least one groove formed in said hub structure; and
    b) at least one non-linear suturing needle slidably disposed in said groove and being sharp on an end thereof;
    wherein motion of said suturing needle in a first direction in said groove causes said sharp end to follow a path through said patient's skin.

4. A catheter hub in accordance with claim 3 wherein said at least one groove is circular and wherein said non-linear suturing needle and said path are circular.

5. A catheter hub in accordance with claim 3 wherein said hub structure includes a flat side included in a planar boundary of said hub structure and wherein said circular path passes through said planar boundary at least once.

6. A catheter hub in accordance with claim 4 wherein the axis of said circular groove is coaxial with said central opening axis.

7. A catheter hub in accordance with claim 4 wherein the axis of said circular groove is transverse of said central opening axis.

8. A catheter hub in accordance with claim 7 wherein said circular groove is a first circular groove, and further comprising a second circular groove in said hub structure coaxial with said first circular groove and opposite said central opening axis, and wherein said circular needle includes first and second circular needle portions disposed respectively in said first and second circular grooves and connected by a tang.

9. A catheter system for disposing a catheter tube through the skin of a patient and into a blood vessel, comprising:
   a) a catheter hub structure having a hub axis and a central opening, said hub being coaxially joinable to said catheter tube, and said opening allowing passage of fluids therethrough during use of said catheter hub and said catheter tube, said hub structure including a solid suturing needle slidably rotatable on said hub structure for attaching said hub structure to a portion of said patient's skin, said suturing needle forming more than 180° of a full circle such that said suturing needle is permanently disposed on said hub structure; and
   b) a flexible catheter tube cooperative with coaxially joined to said hub structure.

10. A catheter system in accordance with claim 9 wherein said suturing needle is non-linear.

11. A catheter system in accordance with claim 10 comprising:
   a) at least one groove formed in said hub structure; and
   b) at least one non-linear suturing needle slidably disposed in said groove and being sharp on an end thereof;
   wherein motion of said suturing needle in a first direction in said groove causes said sharp end to follow a path through said patient's skin.

12. A catheter system in accordance with claim 11 wherein said at least one groove is circular and wherein said non-linear suturing needle and said path are circular.

13. A catheter system in accordance with claim 9 further comprising an installation needle for assisting in emplacing said catheter tube into said blood vessel.

14. A catheter system in accordance with claim 9 further comprising a wire extending through said hub structure for assisting in emplacing said catheter tube into said blood vessel.

* * * * *